(12) United States Patent
Stephenson et al.

(10) Patent No.: US 12,702,869 B2
(45) Date of Patent: Aug. 11, 2026

(54) ULTRASONIC AURICULAR VAGUS NERVE STIMULATOR USING CANNABINOID-CONTAINING COUPLING FLUID

(71) Applicant: NeurGear, Inc., Rochester, NY (US)

(72) Inventors: Stanley Ward Stephenson, Spencerport, NY (US); Jonathan Taylor Hacker, Rochester, NY (US); Andrew Robert Slegaitis, Forestport, NY (US)

(73) Assignee: NeurGear, Inc., Rochester, NY (US)

( * ) Notice: Subject to any disclaimer, the term of this patent is extended or adjusted under 35 U.S.C. 154(b) by 0 days.

(21) Appl. No.: 19/302,941

(22) Filed: Aug. 18, 2025

(65) Prior Publication Data

US 2025/0381420 A1 Dec. 18, 2025

Related U.S. Application Data

(63) Continuation-in-part of application No. 18/631,192, filed on Apr. 10, 2024.

(Continued)

(51) Int. Cl.

*A61N 7/00* (2006.01)
*A61M 35/00* (2006.01)
*H04R 1/10* (2006.01)

(52) U.S. Cl.

CPC ............... *A61N 7/00* (2013.01); *A61M 35/10* (2019.05); *H04R 1/1008* (2013.01);

(Continued)

(58) Field of Classification Search

CPC . A61N 7/00; A61N 2007/0026; A61M 35/10; A61M 2210/0662; H04R 1/1008; H04R 1/1075

See application file for complete search history.

(56) References Cited

U.S. PATENT DOCUMENTS

| | | | |
|---|---|---|---|
| 6,776,757 | B2 | 8/2004 | Larson et al. |
| 10,011,804 | B2 | 7/2018 | Mancosky |

(Continued)

FOREIGN PATENT DOCUMENTS

| | | | | |
|---|---|---|---|---|
| AU | 2021203916 A1 | 7/2021 | | |
| CA | 2938621 A1 | 6/2016 | | |
| WO | WO-2021003393 A1 * | 1/2021 | ........... | A61K 31/658 |

OTHER PUBLICATIONS

Verma N. et al., Auricular Vagus Neuromodulation—A Systematic Review on Quality of Evidence and Clinical Effects, Apr. 29, 2021, Frontiers in Neuroscience, vol. 15—2021, DOI=10.3389/fnins.2021.664740, 1662-453X https://www.frontiersin.org/journals/neuroscience/articles/10.3389/fnins.2021.664740 (Year: 2021).*

*Primary Examiner* — Joel Lamprecht
*Assistant Examiner* — James F McDonald, III
(74) *Attorney, Agent, or Firm* — ePatentManager.com; Guerry L. Grune

(57) ABSTRACT

A headset apparatus for a user comprising an ultrasound transducer mounted to the headset apparatus, wherein the ultrasound transducer is configured to press against the auricular vagus nerve, a coupling fluid on the surface of the transducer permitting ultrasonic energy to pass into human skin and, a cannabinoid extract in solution with the coupling fluid.

18 Claims, 13 Drawing Sheets

Related U.S. Application Data

(60) Provisional application No. 63/731,875, filed on Jun. 18, 2024, provisional application No. 63/577,988, filed on Jun. 12, 2023, provisional application No. 63/458,771, filed on Apr. 12, 2023.

(52) U.S. Cl.
CPC ... *H04R 1/1075* (2013.01); *A61M 2210/0662* (2013.01); *A61N 2007/0026* (2013.01)

(56) References Cited

U.S. PATENT DOCUMENTS

| | | | | |
|---|---|---|---|---|
| 10,064,950 | B2 | 9/2018 | Naheed | |
| 10,413,757 | B2 | 9/2019 | Sato et al. | |
| 2005/0143787 | A1 * | 6/2005 | Boveja | A61N 1/36007<br>607/45 |
| 2015/0132409 | A1 * | 5/2015 | Stein | A61K 31/405<br>424/665 |
| 2018/0021564 | A1 * | 1/2018 | Goodall | A61N 2/002<br>600/379 |
| 2018/0064728 | A1 * | 3/2018 | Chang | A61K 31/57 |
| 2019/0240468 | A1 * | 8/2019 | Yun | A61N 1/3606 |
| 2019/0275322 | A1 * | 9/2019 | Cartledge | A61N 1/3603 |
| 2020/0222708 | A1 * | 7/2020 | Simon | A61N 1/3601 |
| 2022/0062621 | A1 * | 3/2022 | Hogg | A61N 1/36014 |

* cited by examiner

ULTRASONIC AURICULAR VAGUS NERVE STIMULATOR USING CANNABINOID-CONTAINING COUPLING FLUID

CROSS REFERENCE TO RELATED APPLICATIONS

This application is a nonprovisional conversion of and claims priority to U.S. Provisional Application 63/731,875 filed Jun. 18, 2024, the entirety of which is incorporated by reference herein.

This application is also a continuation-in-part of and claims priority to U.S. Nonprovisional application Ser. No. 18/631,192 filed Apr. 10, 2024, which is a nonprovisional conversion of U.S. Provisional Application No. 63/458,771 filed as a provisional patent application on Apr. 12, 2023, entitled "ULTRASONIC AURICULAR VAGUS NERVE STIMULATOR" and also a nonprovisional conversion of U.S. Provisional Application No. 63/577,988 filed as a provisional patent application on Jun. 12, 2023, entitled "DRIVE FOR ULTRASONIC AURICULAR VAGUS NERVE STIMULATOR", the entirety of which are incorporated herein in their entirety.

FIELD OF THE INVENTION

The present disclosure relates generally to therapeutic stimulation using ultrasonic radiation and more particularly to ultrasound stimulation of the vagus nerve at the ear and coupling methods between ultrasonic transducers and a user.

BACKGROUND OF THE INVENTION

In human anatomy, the vagus nerve is the tenth cranial nerve that relays sensory and motor information between the brain and organs in the chest and abdomen. The auricular branch of the vagus nerve lies within the tissue of both outer ears, as represented in the schematic view of FIG. 1, with representative portions of vagus nerve branches shown in enlarged the inset K. The vagus nerve V is considered part of the parasympathetic nervous system regulating and responding to conditions related to rest and digestion of the human user. Stimulation of the vagus nerve, such as electrical stimulation, is widely held to improve overall well-being of the user.

Vagus nerve stimulation has been approved by the Food and Drug Administration (FDA) to treat some forms of epilepsy, as well as depression. For some conventional methods of vagus nerve stimulation (VNS) treatment, healthcare providers implant a small electrical device in the chest, under the skin, to send mild, painless electrical signals through the left vagus nerve to the brain. These impulses can be shown helpful in calming irregular electrical activity in the brain.

There is accumulating evidence to suggest that vagus nerve stimulation can help to quell inflammation related to a number of other autonomic or inflammatory disorders, which would make it useful for a wide range of adult and pediatric patients.

In some early therapeutic work for neural stimulation, a set of conductive pads was attached to the body and a control mechanism to apply transdermal electrical shocks to a patient's limbs. A series of DC pulses can be applied to an area for a given period of time. In this sequence, a second time period with no stimulation passes, then a third interval of stimulation occurs, with reversed DC voltage. This process was shown to alleviate pain very rapidly.

Other earlier work discloses use of electrical shock to the auricular vagus nerve. In one embodiment, non-invasive electrodes are mounted on skin surfaces in the ear. One electrode is placed outside the ear conch and the second electrode is placed in the external auditory canal, implanted to excite the vagus nerve. A controller is connected to an electrical stimulation circuit and is adapted to provide vagus nerve stimulation. A feedback circuit based on physiological response can control the applied stimulation. The use of electrical shock, however, can be uncomfortable and can lead to neural scarring that reduces therapeutic value.

Still other work discloses modulating neural activity by using a reversible blocking condition of peripheral neural structures. The reversible blocking process is applied when the user is in a first state, and deactivated when the user is in a second state. External sensing components are used to detect neural activity and control the blocking energy. Certain embodiments disclose implanted sensors and antennae to sense and conduct therapeutic energy. Such types of apparatus can be applied over the surface of the extremities, including arms, legs, and fingers. However, the vagus nerve is embedded deeply into the neck, so that such a method can require surgical procedure in order to be reached with sufficient electrical signal.

In one earlier, non-invasive method of exciting the vagus nerve, the user presses a set of electrodes to the skin of the neck to provide electrostimulation of the Vagus nerves. The stimulation device interconnects with apparatus that records the therapy session. The information can be provided to medical personnel to monitor the therapeutic regime. The apparatus applies electrical energy in the form of an AC sinewave that is applied over periodic time intervals. However, contact pressure factors are not well-defined and providing sufficient electrical stimulation to stimulate the vagus nerve can be painful for the user.

More recent work has applied focused ultrasonic energy for peripheral nerve modulation. Ultrasound is used to locate a nerve within tissue. The nerve is then stimulated by focused ultrasound in order to modulate peripheral nerves, such as nerves in arms or legs. The ultrasound probe can use an imaging process to observe tissue deformation due to the focused ultrasound energy.

Another more recent apparatus is attached to the user's head for stimulating the auditory system. An ultrasound transmitter is held to the exterior of the head to focus ultrasound onto the cochlea, which is located deeply into the skull. An embodiment shows the device is located on the temple near the external ear canal and oriented to direct energy to the cochlea. Multiple transducers can be located on the headband for stimulation. In an embodiment, a plug is inserted into the ear canal and excited by a device housed behind the ear. The device within the ear canal emits ultrasonic radiation radially into the skull. The apparatus receives audible sound, translates that sound into one or more ultrasonic frequencies and directs the ultrasonic radiation at those frequencies to the cochlea to create a perception of sound to the user.

In yet other work, a garment supports a stimulating device for the user. The particular stimulation devices can include vibration or audible sound to effect positive therapy. The garment can cover the user's chest, abdomen, arms or legs. In one embodiment, an acoustic speaker is supported on a frame that directs sound energy towards the user head. Other embodiments disclose a single speaker located on the user's body. The stimulation devices are disclosed as providing acoustic, vibration, or electrical pulses delivered through contact with the skin. The stimulators are activated in response to external command from such sources as smart phone or computer games, for example.

Among other devices and configurations for stimulating the auricular vagus nerve, one approach uses a wearable neural stimulation device attached to the ear. The neural stimulator can use any type of energy, including mechanical, electrical, magnetic, ultrasound, optical, thermal or chemical energy. The supporting frame can support multiple stimulators in various areas of the ear. In one embodiment, the stimulation occurs in both ears through stimulators supported by a single frame. A member wraps around the back of the ear to secure the device to the ear and a neural stimulator operates in response to commands for a processor. The processor receives commands from a remote communication system. An audio speaker can be incorporated to provide audio information to the user.

Ultrasound therapy has been applied to muscle tissue to ease pain. An ultrasound transducer can provide mild heat and pulsed mechanical pressure to ease pain in muscles. The ultrasound transducer is typically coupled with an ultrasound fluid or gel to improve energy transmission to the afflicted tissue. The coupling gel is formulated to have physical properties similar to water. The coupling medium can be a gel, a thick, conductive substance that's typically made of water with a viscosity increasing agent, such as propylene glycol. Propylene glycol is a synthetic compound that's often found in food, cosmetics, and hygiene products. Other thickeners that may be found in ultrasound gel include glycerin, Carbomer, Sodium Hydroxide, Diazolidinyl Urea, Methylparaben, Disodium EDTA, Propylparaben coconut, and hemp fluid.

*Cannabis* fluids are insoluble in water, but are soluble in fluids and solvent. *Cannabis* fluids can be extracted from pulped *cannabis* plants with heat or solvents. Ultrasound can also be used to extract cannabinoids from hemp directly, such as the Hielscher Ultrasonicator UP400St. The Ultrasonicator UP400St applies ultrasound to hemp in water to extract and separate *cannabis* fluids. The high intensity ultrasound coagulates and separates the fluid from the plant fiber and aqueous components of the hemp plant.

*Cannabis* extracts have been found to be therapeutic when applied to and absorbed through the skin into the body. *Cannabis* extracts can include various chemical structures, such as the CBDs and THCs. The various molecules in general have a calming effect. Various fluids or suspensions are commercially available that can be applied to areas of bodies to relieve tension. The extracts can be dispersed *cannabis* fluid particles in water or *cannabis* extracts in solution with a solvent agent. *Cannabis* in such fluids can be in concentrations of between 5 and 35 percent. Nearly pure cannabinoids can also be used therapeutically.

It is well known that stimulation of the Vagus nerve can induce wellness. Stimulation of the Vagus nerve can occur in the auricular branch of the nerve using electrical stimulation, and our prior application discloses apparatus for stimulating the auricular branch of the vagus nerve using ultrasound. The ultrasonic therapy can be enhanced by the use of a coupling fluid between the transducer and the user's skin. Therapy can be further improved by the application of coupling fluid containing or consisting entirely of cannabinoids.

SUMMARY OF THE INVENTION

It is an object of the present disclosure to advance the art of stimulating the vagus nerve. Embodiments of the present disclosure provide non-invasive and readily usable vagus nerve stimulation with an apparatus that provides ultrasound energy to the auricular vagus nerve.

With this object in mind, the present disclosure provides a headset apparatus for a user to wear comprising:

(a) an ultrasound transducer mounted to the headset apparatus, wherein the ultrasound (b) transducer is configured to press against an auricular vagus nerve, (b) a coupling fluid on a surface of the ultrasound transducer that provides ultrasonic energy to pass into human skin and, (c) a cannabinoid extract in solution with at least one coupling fluid.

In some cases, the coupling fluid is a solution that contains cannabidiol (CBD).

In addition the coupling fluid can be a solution that contains tetrahydrocannabinol (THC) with at least one carrier wherein the carrier is a coupling fluid, water, glycerine, and/or a combination of coupling fluid, water, glycerine and one or more emulsifiers.

Often, the coupling fluid is a solution that contains cannabinol as a terpene.

Here, the cannabinoid is in solution with at least a second component.

Often, the cannabinoid is in solution with one or more vegetable fluids.

The *cannabis* containing fluid can be incorporated into a conformal pad.

It is possible for the *cannabis* conformal pad to be selectively removable from the apparatus.

In another embodiment, a method for using a headset apparatus adjustable for one or more users to wear comprises;

(a) providing an ultrasound transducer mounted to the said headset apparatus, wherein the ultrasound transducer is configured to press against an auricular vagus nerve of the one or more users, (b) a coupling fluid on a surface of the ultrasound transducer that provides ultrasonic energy to ensure the passing of the ultrasonic energy into human skin and, (c) using a cannabinoid extract in solution with the at least one coupling fluid so that when the user utilizes the headset apparatus the ultrasound energy in combination with the cannabinoid extract provides the one or more users an ability to overcome mental and/or physical ailments.

In some embodiments the coupling fluid is a solution that contains cannabidiol (CBD).

In yet another embodiment the coupling fluid is a solution that contains tetrahydrocannabinol (THC) with at least one carrier wherein the carrier is a coupling fluid, water, glycerine, and/or a combination of coupling fluid, water, glycerine and one or more emulsifiers.

The coupling fluid can also be a solution that contains cannabinol as a terpene.

In addition, the cannabinoid can be in solution with at least a second component.

Often the cannabinoid is found in solution with one or more vegetable oils/fluids.

In another embodiment the *cannabis* containing fluid is incorporated into a conformal pad.

Here, the user of the *cannabis* conformal pad can selectively remove the conformal pad from the headset apparatus.

These objects are given only by way of illustrative example, and such objects may be exemplary of one or more embodiments of the disclosure. Other desirable objectives and advantages inherently achieved by the disclosed disclosure may occur or become apparent to those skilled in the art. The invention is defined by the appended claims.

BRIEF DESCRIPTION OF DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
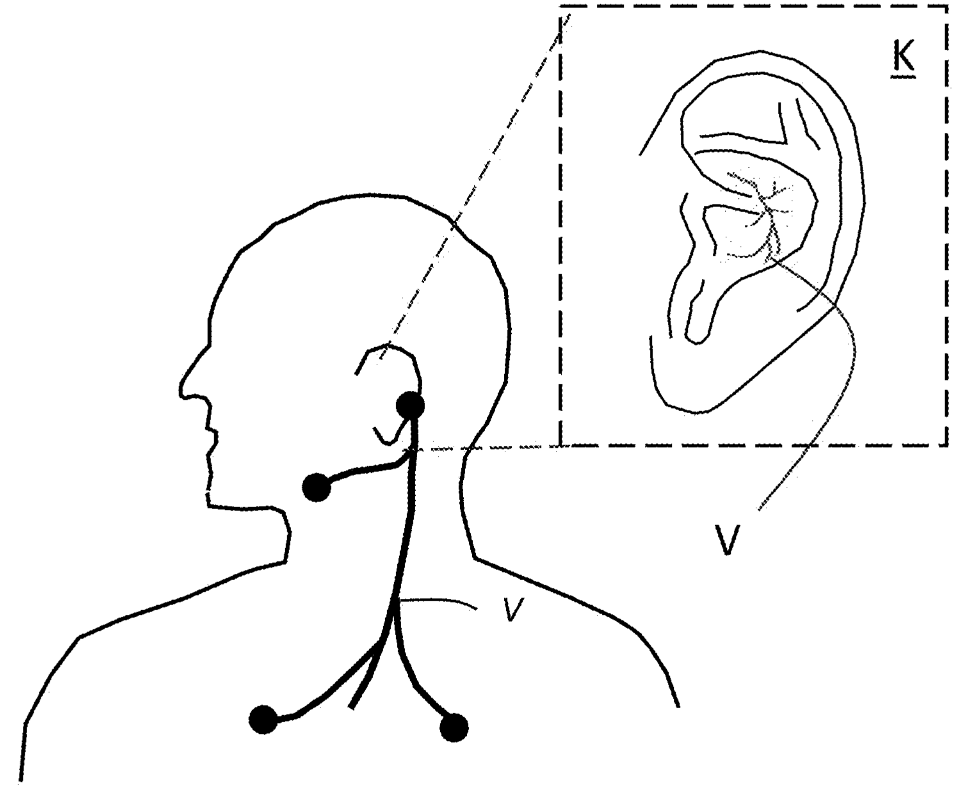
FIG. 1 is a schematic view showing a portion of the path of the auricular vagus nerve in the upper part of the anatomy.

Figures provided herein are given in order to illustrate principles of operation and component relationships according to the present invention and may not be drawn with intent to show actual size or scale. Some exaggeration may be necessary in order to emphasize basic structural relationships or principles of operation. Some conventional components that would be needed for implementation of the described embodiments, such as support components used for providing power, for packaging, for interconnection, and for mounting, for example, may not be shown in the drawings in order to simplify description of the invention. In the drawings and text that follow, like components are designated with like reference numerals, and similar descriptions concerning components and arrangement or interaction of components already described may be omitted.

Where they are used, the terms "first", "second", and so on, do not necessarily denote any ordinal or priority relation, but may be used for more clearly distinguishing one element or time interval from another. The term "plurality" means at least two.

In the context of the present disclosure, the term "energizable" describes a component or device that is enabled to perform a function upon receiving power and, optionally, upon also receiving an enabling signal.

In the context of the present disclosure, positional terms such as "top" and "bottom", "upward" and "downward", and similar expressions are used descriptively, to differentiate different surfaces or views of an assembly or structure and do not describe any necessary orientation of the assembly in an apparatus. When used with respect to human anatomy, these terms relate to a user in normal standing or seated posture.

In the context of the present disclosure, the term "coupled" is intended to indicate a mechanical association, connection, relation, or linking, between two or more components, such that the disposition of one component affects the spatial disposition of a component to which it is coupled. For mechanical coupling, two components need not be in direct contact, but can be linked through one or more intermediary components.

The terminology "in signal communication" as used in the present application means that two or more devices and/or components are capable of communicating with each other via signals that travel over some type of signal path. Signal communication may be wired or wireless. The signals may be communication, power, data, or energy signals which may communicate information, power, and/or energy from a first device and/or component to a second device and/or component along a signal path between the first device and/or component and second device and/or component. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "about" indicates that the value listed can be somewhat altered, as long as the alteration allows a component or assembly to be in reasonable conformance with the process or structure of the illustrated embodiment. The term "exemplary" is not intended to be limiting, but indicates an illustrative example, rather than implying an ideal.

In the context of the present disclosure, the term "ultrasound" refers to acoustic vibration frequencies above 20 KHz. In ultrasound stimulation, acoustic waves of mechanical energy are generated and used to apply pressure to nerve tissue. With tactile stimulation from ultrasound energy, the resulting pressure changes in intracellular and extracellular fluid appear to change cell membrane curvature and generate flexoelectric effects that propagate along the nerve tissue.

Research strongly suggests that pulsed pressure, with intervals of movement and rest, can be beneficial for allowing biochemical recovery during stimulation.

Figure 2:
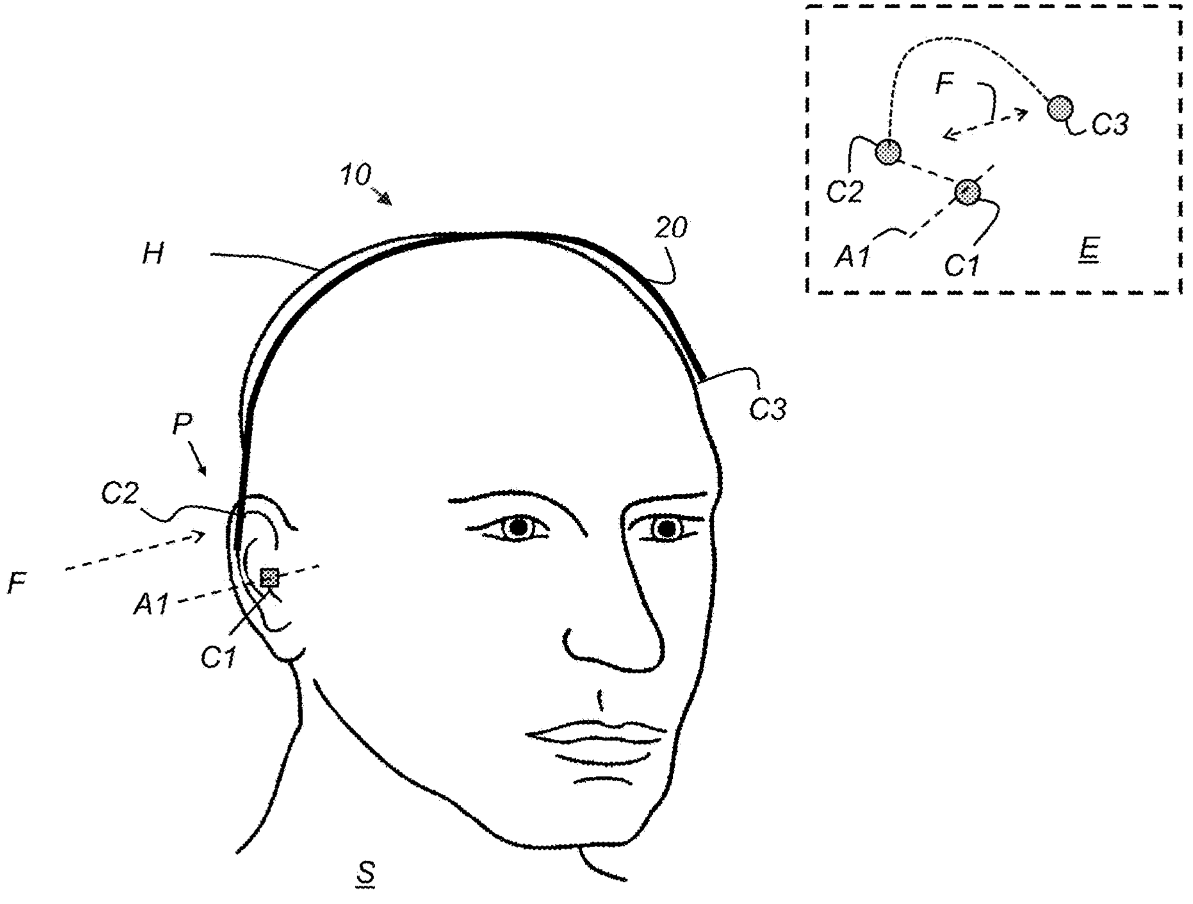
FIG. 2 is a schematic view that shows anatomical features of interest for proper mounting and positioning of an ultrasound stimulator apparatus for the pinna.

Referring to FIG. 2, the Applicant has found that the pinna P surface of the human ear can provide a useful access point for vagus nerve stimulation. Nerve portions of an auricular branch of the vagus nerve lie just under the pinna P surface of both ears, as shown in FIG. 1, and extend from there inward, toward other anatomy, including the brain. Some of the more accessible nerve fibers extending from the vagus nerve lie in the central depression of pinna P, the concha of the ear.

To provide a suitable device for stimulation of the vagus nerve at the pinna, wherein the device is suitable for consumer use, the Applicant as addressed a number of aspects that have not been met by any proposed solution, including:

- Lightweight and compact, with the ultrasound source self-contained;
- No requirement for external cabling, such as for signal, power;
- Hands-free operation;
- Self-aligning, with effective stimulation, not requiring setup and installation by a specialist;
- Adaptable for use by users of all ages and sizes;
- Easily worn and comfortable to use; and
- Relatively inexpensive.

In developing a hands-free apparatus 10 to stimulate nerve endings using ultrasound energy, it is important to position the stimulus appropriately, so that the ultrasound signal is most effective. However, the Applicant has found that, for most users, ultrasound stimulation applied to the pinna P of the ear can be difficult or impossible for the wearing user S to perceive. That is, unlike apparatus that apply other forms of stimulating energy, ultrasound apparatus provides no clear-cut, intuitive clues for the user to ascertain and guide proper placement of the signal source of apparatus 10 against the skin surface. For design of a wearable device, this means that the wearer can't be expected to adjust device positioning and alignment to achieve the best results. Moreover, in order for the ultrasound stimulation to be effective, sufficient nesting force F must be applied to urge the transducer firmly enough against the skin without causing discomfort. Otherwise, without proper position and nesting pressure, even when the ultrasound device is energized, the emitted signal may not be well-directed and therefore could be ineffective in providing therapeutic benefit.

The problem of achieving proper placement with suitable applied pressure against the pinna is further complicated by the variability of anatomy among the user population. Head sizes and dimensions of various features in and around the ears can vary significantly. Some measure of adaptability is needed in order to provide the needed placement and pressure and to accommodate anatomical differences with a single design.

The Applicant's apparatus 10 is designed to employ a pattern of constraints for stimulus placement with sufficient degrees of freedom to accommodate and benefit a broad population of users. Referring to FIG. 2, there are shown three contact surfaces around which the constraint pattern is based. Two of the contact surfaces are at the ear:

(i) the ear canal C1, which defines a reference axis A1 for alignment of the Applicant's stimulator apparatus;

(ii) the pinna P surface C2, in the neighborhood of the superior crus of the antihelix, very near the cymba conchae, providing the surface contact through which the stimulator apparatus applies the ultrasound signal;

A third surface C3 lies along the forehead of user S, opposite surface C2, or, alternately, at the opposite ear, and provides a fixed base surface that, in conjunction with a curved flexure 20, applies a nesting force F against pinna P at the antihelix. Nesting force F, provided by deflection of flexure 20, can have a value over a broad range; according to an embodiment of the present disclosure, nominal force F is in the range of about 135 grams. A force of this exemplary magnitude over a 12 mm contact surface yields pressure of 0.83 g per mm2 for energy transfer. It should be noted that increasing the force beyond such a value may not increase the energy transfer efficiency, and that, for some individuals, reduced force F levels, such as reduction by about 50 g, may be suitable. Headset apparatus 10 can be designed to apply a higher force value in order to accommodate the full range of wearer head sizes.

An inset E in FIG. 2 shows the schematic arrangement of the three contact surfaces C1-C3 and their relation to axis A1. The relative distance between contact surfaces C1/C2 and opposing contact surface C3 can vary per user S, with nesting force F tension provided by curved flexure 20. Some measure of additional adjustability for contact surfaces is also available, as described in more detail following.

Figure 3:
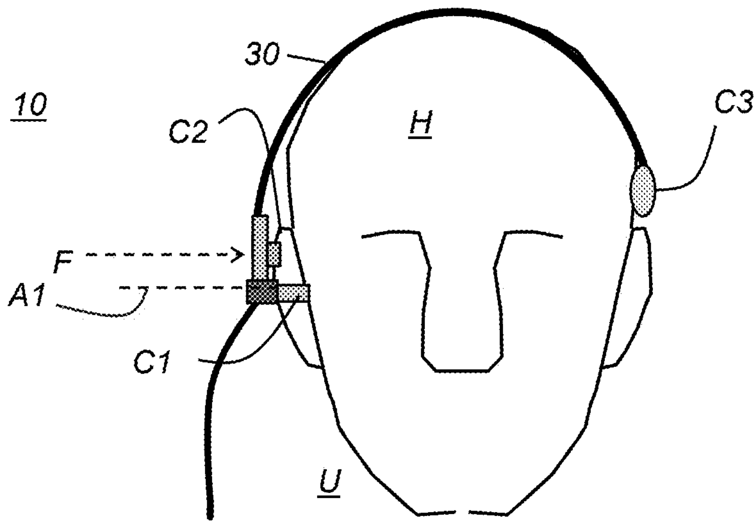
FIG. 3 is a front plan view of a stimulator apparatus on the head of a user.

FIG. 3 is a front view of a stimulator apparatus 10 configured as headwear for stimulating an auricular vagus nerve of a user U using the three noted contact surfaces C1-C3, in accordance with an embodiment of the present disclosure. Apparatus 10 seats atop the head H of user U and is poised against head H anatomy in order to dispose its emissive components in suitable position, and with suitable force, against the user's ear. According to an embodiment, a headband 30, configured to extend across a parietal region of the head, provides flexure 20.

Figure 4:
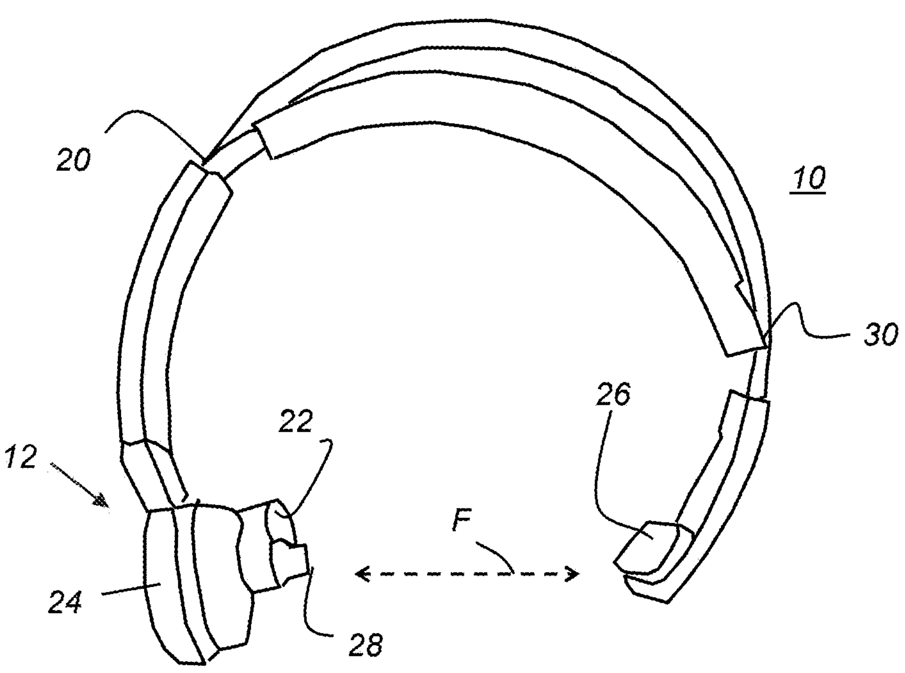
FIG. 4 is a perspective view of a stimulator apparatus according to an embodiment of the present disclosure.

Referring to the perspective view of FIG. 4, a stimulator headset apparatus 10 in accordance with the present disclosure includes an ultrasonic transducer 22 provided on a headset. The headset has a frame 24 in the position of the headset "earpiece", that is, in the position of the component that is intended for positioning against the ear; an earpiece 12 is labeled in FIGS. 4 and 5. For clarity, frame 24 is referred to herein as being in the earpiece 12 position of headset 30.

In the context of the present disclosure, relative to headsets, the term "earpiece" is used as a convenient term that readily identifies the position of components that the headset apparatus 10 seats against the ear of user U. Earpiece 12 comprises frame 24 components of the Applicant's device, along with any hardware and fixtures that are used to properly position frame 24 and its components suitably for ultrasound stimulation, as described in more detail herein. There may or may not be additional audio speakers within earpiece 12 in various embodiments.

Frame 24 provides a housing for the signal emission components that positions stimulating components suitably against the ear. Within frame 24, transducer 22 is formed by shrouding a contact side of a piezoelectric element within a conformal surface, such as silicone, that transmits ultrasound; silicone also provides a measure of friction for holding transducer 22 in position against the skin surface. A contact pad 26, at the opposite end of flexure 20, provides the needed nesting force F that urges transducer 22 into its position against the pinna P. An alignment feature 28, spaced apart from transducer 22, seats within ear canal C1 to provide alignment that allows proper positioning of transducer 22 against the pinna P surface.

Thus, using its combination of alignment feature 28, transducer 22, and contact pad 26, along with tension provided through curved flexure 20, stimulator apparatus 10 provides the needed 3-contact positioning and nesting force for locating signal emission where it is effective, and for maintaining this position without requiring user S to make more than rudimentary adjustments to suit individual anatomy.

Figure 5:
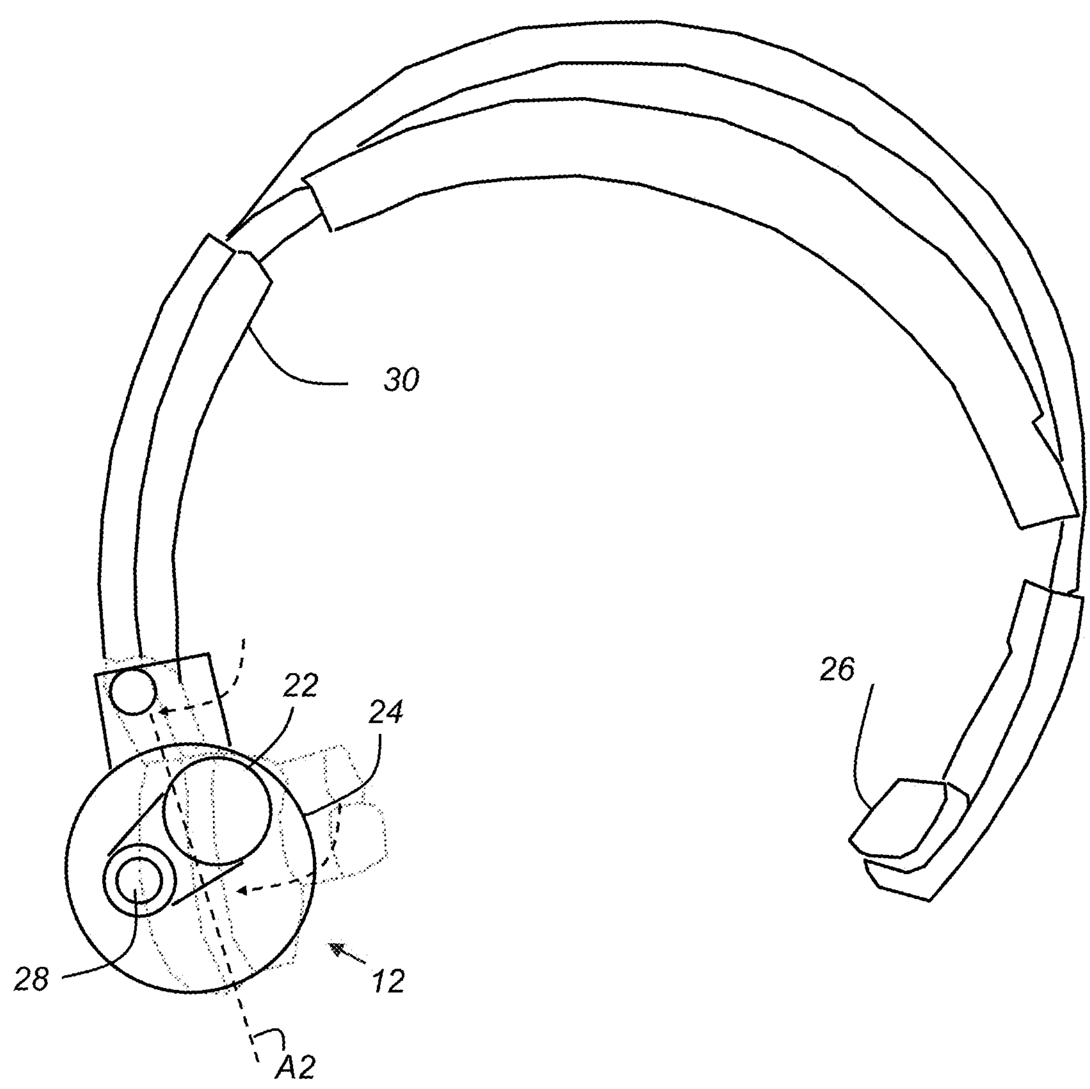
FIG. 5 is a perspective view of a stimulator apparatus according to an alternate embodiment of the present disclosure.

According to an alternate embodiment of the present disclosure, an additional adjustment can be provided for adapting the angle of the pair of contact surfaces C1 and C2 to the head. The perspective view of FIG. 5 shows rotation of frame 24 about an axis A2 that can be projected from the end of the headband of flexure 20, substantially parallel to the transducer 22 surface.

Figure 6:
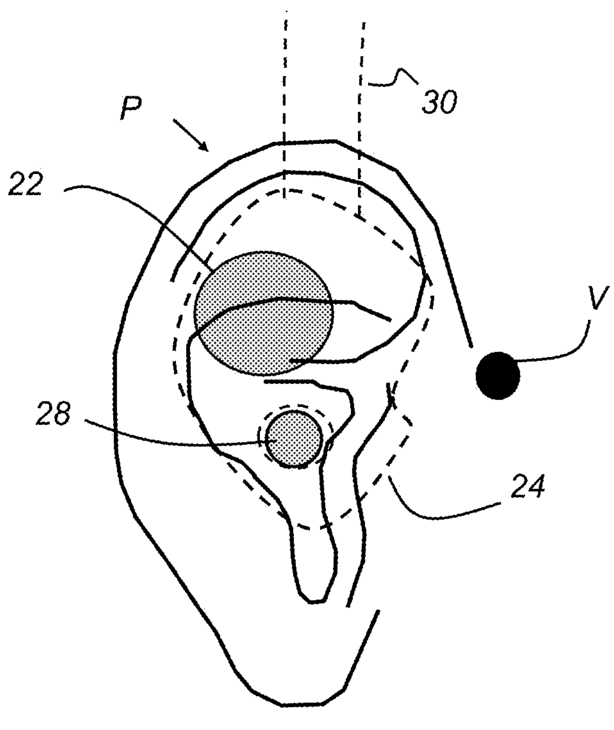
FIG. 6 is a side view showing relative positions of transducer and alignment feature components according to an embodiment of the present disclosure.

Headband 30 for providing flexure 20 can be formed from metal and/or plastic or other materials and is configured to flex when positioned across the top of the head 10, extending generally over the parietal or parietal/frontal region. Force F is applied against contact pad 26 for urging transducer 22 against the pinna P surface. Contact pad 26 can be a compressive foam or other cushioning material for comfort of the user S. As shown in the plan view of FIG. 6, transducer 22 is positioned and aligned within the concha area of pinna P by alignment feature 28 that is configured to extend into ear canal C1. Frame 24, shown in outline in FIG. 6 to allow visibility of transducer 22 and alignment feature 28, holds transducer 22 and alignment feature 28 in fixed position relative to each other. FIG. 6 also shows the relative position of vagus nerve V, with branches (not shown) extending into pinna P.

Figure 7:
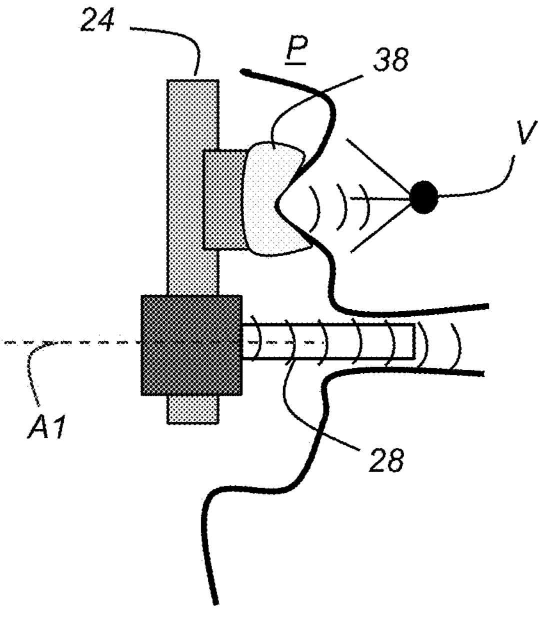
FIG. 7 is a cross-sectional side view that shows relative positions of components at the ear.

FIG. 7 is a cross-sectional side view that shows relative positions of frame 24 components at the ear. Conformal pad 38 of transducer 22 is pressed against pinna P, defining contact surface C2 as described previously, to transmit the stimulating ultrasound energy. Alignment feature 28 can be a molded pin that seats at least partially within ear canal to provide contact surface C1.

According to an embodiment of the present disclosure, an optional audio signal can be provided to user U through alignment feature 28, acting as an audio "earpiece" as represented in FIG. 7. This audible signal can help to assure user U that the ultrasound transducer 22 is being energized and actuated and that the ultrasound signal, otherwise imperceptible to the user in many cases, is being emitted.

Figure 8:
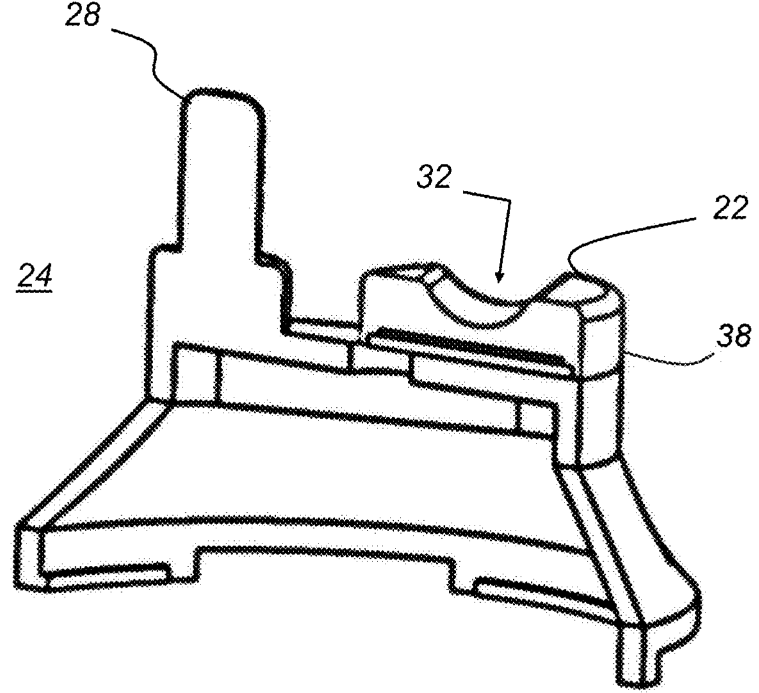
FIG. 8 is a cross-sectional side view of the frame for positioning and stimulus components.
Figure 9:
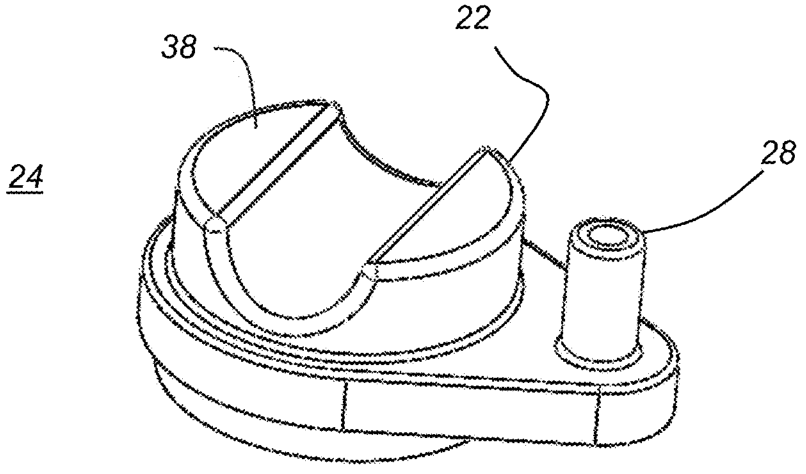
FIG. 9 is a perspective view of the frame for positioning and stimulus components.
Figure 10:
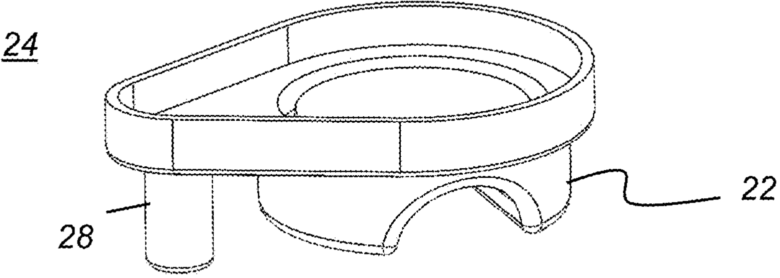
FIG. 10 is a bottom view of the frame for positioning and stimulus components.

FIG. 8 is a cross-sectional side view of frame 24 of the headset 30 that provides a housing for positioning and stimulus components according to an embodiment of the present disclosure. Conformal pad 38 that lies against transducer 22 can have an indent 32 feature for improved conformance at the pinna P surface, thereby improving the coupling of the ultrasound signal. It can be seen that frame 24 can be a unitary piece that provides a housing for additional components at the earpiece position and used to drive the transducer and to provide power, for example. FIGS. 9 and 10 are perspective and bottom views of frame 24. Frame 24 can be molded plastic or other materials. Conformal pad 38 can optionally be a coating or molded fitting applied to a surface of the piezoelectric actuator.

Figure 11:
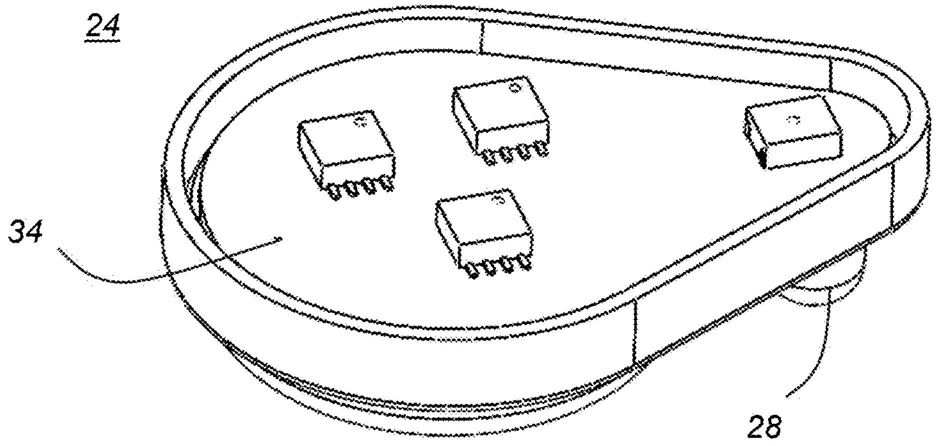
FIG. 11 is a bottom view of a portion of the frame assembly having a circuit board.

FIG. 11 is a bottom perspective view of a portion of the frame 24 assembly having a circuit board 34. Wiring (not shown) can connect circuit board 34 to piezo element 40 in transducer 22.

Figure 12:
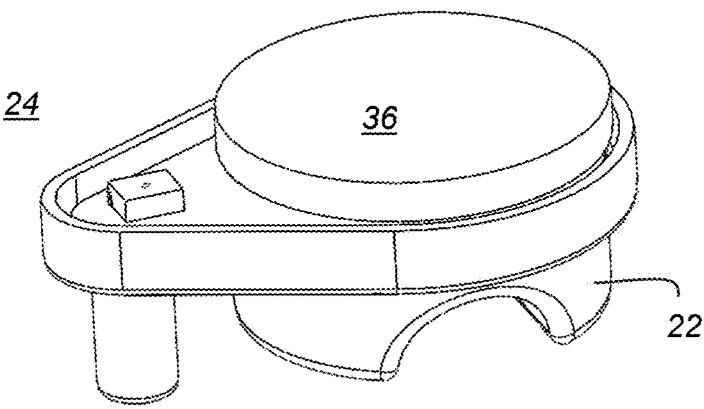
FIG. 12 is s bottom view of a portion of the frame assembly having a replaceable battery.

FIG. 12 is a bottom perspective view of a portion of the frame 24 assembly having a replaceable battery 36.

Figure 13:
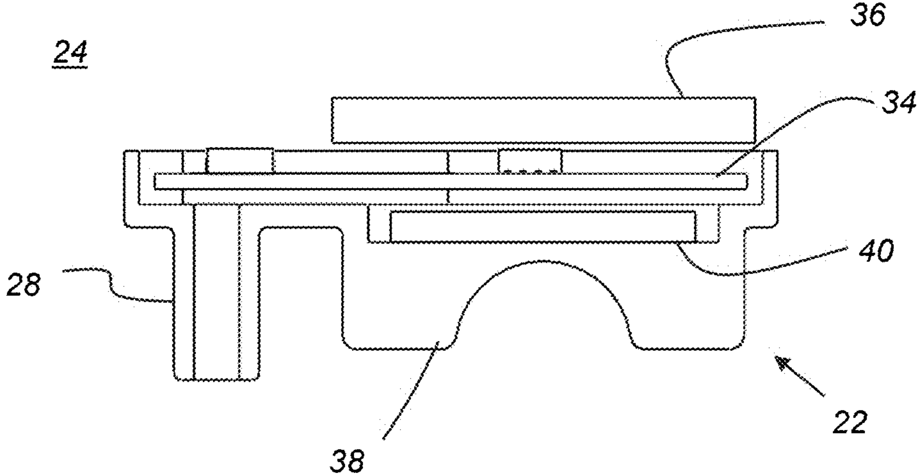
FIG. 13 is a cross-sectional view of the frame assembly.

FIG. 13 is a cross-sectional view of the frame 24 assembly that shows the positions of battery 36 and circuit board 34, along with components of transducer 22, including conformal pad 38 and piezoelectric element 40. Transducer 22 can be epoxied or otherwise coupled to frame 24. According to an embodiment of the present disclosure, piezoelectric element 40 is configured as a plate, having a planar output surface. Frame 24 positioning components are then configured to orient the piezoelectric element 40 so that the planar output surface is substantially parallel to the pinna P surface; piezoelectric element 40 plate is then substantially orthogonal to alignment feature 28, as was shown in FIG. 7, for example.

Conformal pad 38 can be made of an elastomer such as silicone rubber or polyurethane. According to an embodiment, conformal pad 38 is formed from silicone rubber, with a hardness of 20 A Shore durometer. Conformal pad 38 can be molded to be conformal with crux of the ear helix and with the floor of the concha in order to more closely couple ultrasonic energy from transducer 22 through the skin and thence to vagus nerve V endings. Conformal pad 38 can have multiple layers, using materials having suitable acoustical impedance.

Transmission efficiency is a consideration for selection and configuration of conformal pad 38. Acoustic impedance of pad 38 material is determined as a product of material density and speed of sound within the material. According to an embodiment of the present disclosure, silicone rubber has an acoustic impedance value that is conformable to skin tissue at the ear and can have a degree of effectivity without the use of acoustical gel, such as gel materials typically used with conventional ultrasound scanners, for example. Such gels can be water for acoustic coupling combined with a thickening agent to increase the viscosity of the ultrasound gel.

In the invention conformal pad 38 has a surface that contacts skin over the auricular vagus nerve V. Means are disclosed to forcibly urge conformal pad 38 to the skin surface. In the invention, a coupling fluid covers conformal pad 38 to improve ultrasound transmission to vagus nerve V. In the invention, the coupling fluid contains *cannabis* extract to both improve ultrasound transmission and provide additional chemical therapeutic relief to a user.

Coupling agent can be a pure *cannabis* derivative fluid, such as CBD, CBN, THC, or terpenes. The use of such fluids in ultrasound stimulation uses heat from the ultrasound and ultrasonic pulses to improve transmission of the cannabinoids into the area around the auricular vagus nerve V. The coupling fluid can also be an ultrasound fluid such as coconut or hemp fluid with added cannabinoids in solution. Hemp fluid typically contains less than 1 percent cannabinoids and the invention significantly increases the cannabinoid content of the hemp fluid. The *cannabis* derivative can also be incorporated into coupling pad 38. The *cannabis* fluid in coupling pad 38 improves coupling efficiency and provide chemical therapy. Coupling pad 38 with incorporated cannabinoids and other fluids can be a removable member that is replaceable on transducer assembly 22.

Figure 14:
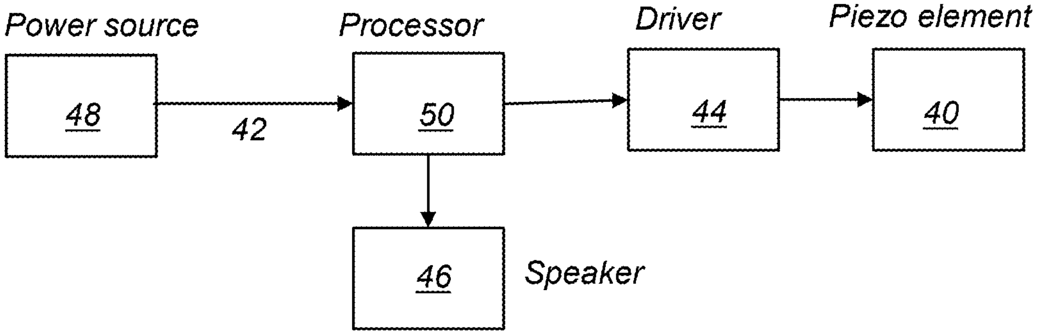
FIG. 14 is a schematic block diagram that shows the interrelated components for generating the ultrasound signal.

Conventional ultrasound equipment can be bulky and require external cabling for routing drive signals to a suitable transducer probe or similar device. In order to provide a wearable device, however, the Applicant's design is scaled to incorporate the power, control logic, drive circuit, and transducer within headset 30 of apparatus 10. FIG. 14 is a schematic block diagram that shows interrelated components for generating the ultrasound signal, according to an embodiment of the present disclosure. A power source 48 provides battery or other electrical energy to the apparatus through a power cable 42. According to an embodiment, power source 48 is a single-use or rechargeable battery contained within the device. According to an alternate embodiment, power source 48 is external, with a power cable 42 routed from the external source 48 to headset 30 or directly to frame 24. Where battery 36 is rechargeable, a charging port can be provided on frame 24. Alternately wireless power transfer can be used for battery re-charging.

A controller 50, such as a microprocessor, is configured to selectively activate a piezo driver 44 to energize piezoelectric element 40 of transducer 22. Controller 50 operates on piezo driver 44 according to a therapeutic regimen, as described subsequently. The waveform generated from driver 44 circuitry excites piezoelectric element 40 to vibrate at a resonant frequency in the ultrasound region.

As noted previously, ultrasound emission lies outside the range of human perception. Thus, it can be impossible for the wearing user S to ascertain whether or not the ultrasound device is operating. An optional speaker 46 can be used to provide an audible signal that indicates active ultrasound emission. Different audible signals, such as different tones, can indicate phases of operation, including start operation, active operation, and end of a therapeutic session. Optionally, the audible indication can be in the form of a spoken statement or one or more acoustic tones. According to an embodiment of the present disclosure, a constant tone between about 30-60 Hz can be used to provide a calming indicator signal that is audible to the wearing user. According to an alternate embodiment of the present disclosure, speaker 46 can provide random noise with various frequency distributions, such as "brown" noise or "green" noise, held to be a variant of white noise, for example. Combining therapeutic aural sound stimulus with ultrasonic stimulation of the vagus nerve can improve the therapeutic effectiveness of apparatus 10.

Figure 15:
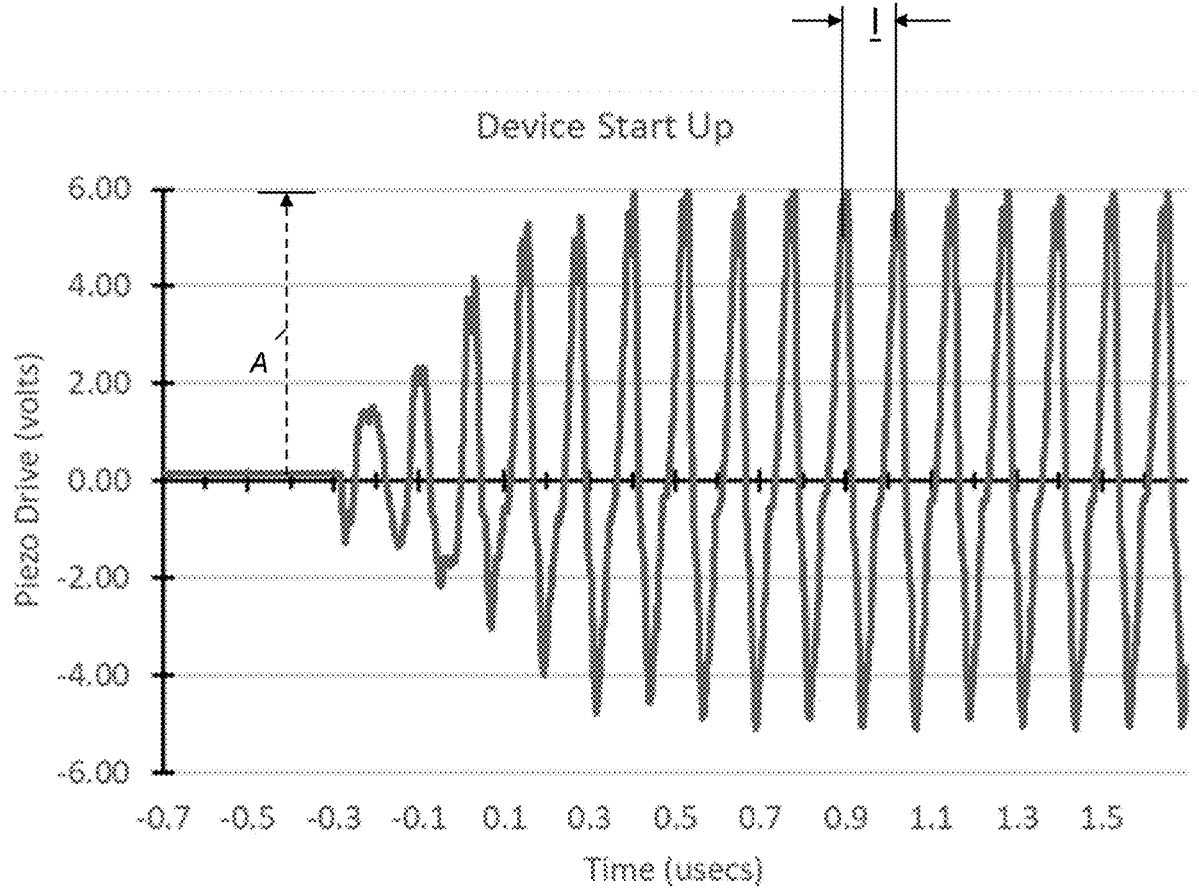
FIG. 15 is a diagram showing aspects of the piezoelectric drive signal.

FIG. 15 is a diagram showing aspects of the piezoelectric drive signal from device startup. Once stabilized, the energizing signal is provided with an amplitude A, at a suitable pulse width and frequency for excitation of piezoelectric element 40. In the embodiment shown, the drive voltage oscillates between about +6.00 and −6.00V. Piezo driver 44 applies voltage to piezoelectric element 40 to generate ultrasound mechanical vibration at frequencies above human hearing range. The vibration frequency, over time interval I, is in the megahertz (MHz) range in order properly excite piezoelectric element 40 and generate a signal that penetrates deeply into pinna P for excitation of vagus nerve V. According to an embodiment of the present disclosure, transducer 22 has a center frequency near 8 MHz, in a range that constrains the ultrasound energy to the auricular vagus nerve area. Signal amplitude A is set to a range of values that excite vagus nerve V without damaging neural tissue.

According to an embodiment of the present disclosure, components in circuit 70 are configured to drive piezoelectric element 40 with a 5V signal at 8 MHz. The plot of FIG. 15 shows voltage response across element 40 over time at application of power to circuit 70. In this embodiment, the drive circuit fully drives the element at the intended frequency in less than 1 microsecond, after about 5 cycles. Drive decays in an equal time period. This rapid startup capability makes circuit 70 suitable for therapeutic regimes in the tens of msec range.

Figure 16:
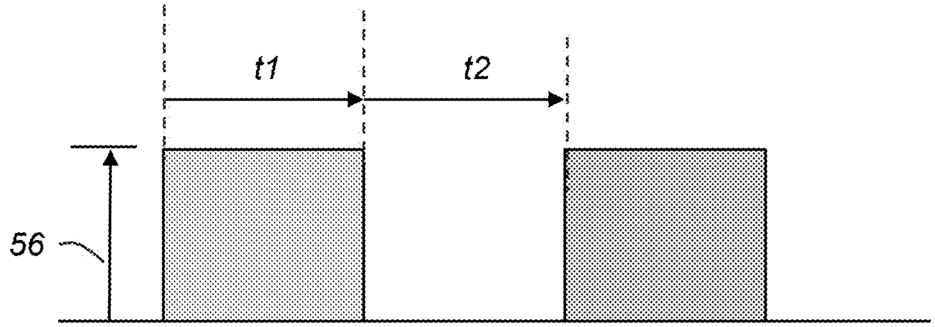
FIG. 16 is a timing diagram that shows energy pulses generated by a controller according to an embodiment of the present disclosure.

FIG. 16 is a timing diagram that shows energy pulses generated by controller 50. During a time period t1, pulses are provided for ultrasound generation and consequent vagus nerve V excitation, with pulse amplitude or power level 56. Controller 50 then turns off the pulse excitation for a time period t2. It is believed that this cycling of excitation between a predetermined power amplitude 56 and zero power provides a therapeutic sequence of excitation and relaxation. During the relaxation period t2, with excitation removed, vagus nerve V will reset biochemically.

According to an embodiment of the present disclosure, a duty cycle of 50% can be used. An excitation time t1 can be set to 30 msec, with relaxation time t2 also set to 30 msec. Repeated cycling between the two states as shown can be executed for a period of time that is held to be therapeutic, such as for 5 minutes, for example. Other t1/t2 timing intervals can be used.

Piezoelectric driver circuit 70 operates efficiently using a minimum number of components and provides a compact oscillator when compared with commercially available products. Circuit 70 can be designed for low-voltage operation, enabling its use with USB-routed power (at 5 V) or battery power (in a range between about 3.3-6 V). Thus, the design shown in FIG. 16B is advantaged over commercially available ultrasound generators, allowing fabrication of a small, light, energy-efficient and portable ultrasound generator that can be comfortably worn by the user, with or without supporting cables.

Piezoelectric element 40 can be formed from any of a number of suitable materials. According to an embodiment of the present disclosure, as was shown in FIG. 13, piezoelectric element 40 can be a piezoelectric plate formed from PZT (Lead zirconate titanate), such as PZT-5A, generally referred to as a piezoelectric ceramic or piezoelectric crystal. Exemplary nominal dimensions for piezoelectric element 40 in plate form can be about 10 mm diameter, 0.28 mm thickness. More generally, piezoelectric materials used for piezoelectric element 40 can be formed from both natural and synthetic materials. Naturally occurring piezoelectric materials include quartz SiO2, berlinite, sucrose, Rochelle salt NaKC4H4O6.4H2O, topaz, and a tourmaline group of minerals. Synthetic piezoelectric materials are further classified as synthetic crystals, ceramics, and polymers. Synthetic piezoelectric crystals include gallium orthophosphate (GaPO4) and langasite (La3Ga5SiO14). Synthetic piezoelectric ceramics include barium titanate (BaTiO3), lead titanate (PbTiO3), lead zirconate titanate, potassium niobate (KNbO3), lithium niobate (LiNbO3), lithium tantalate (LiTaO3), sodium tungstate (NaWO3), zinc oxide (ZnO), aluminium nitride (AlN), and scandium-aluminum nitride. Synthetic piezoelectric polymers can include materials such as polyvinylidene fluoride (PVDF) and copolymers of vinylidene fluoride (VDF) with trifluoroethylene (TrFE), or with tetrafluroethylene (TeFE).

Figure 17:
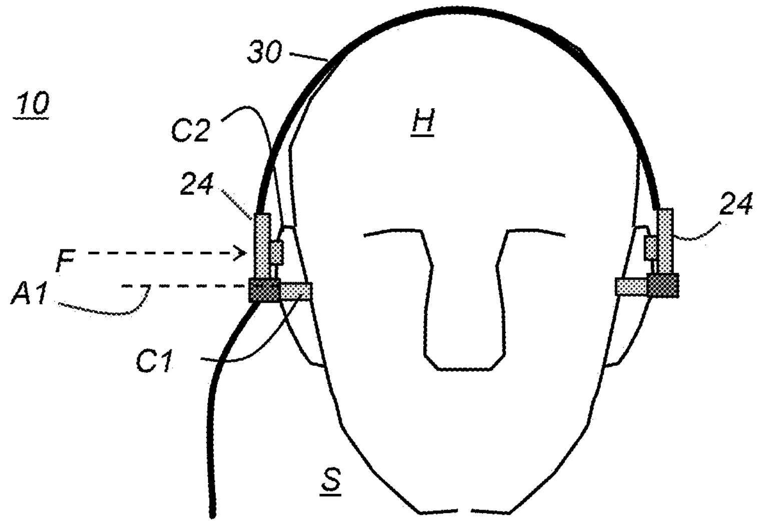
FIG. 17 shows a headset in an alternate embodiment that provides a pair of ultrasound emitters.

FIG. 17 shows a headset in an alternate embodiment that provides a pair of ultrasound emitters. In the FIG. 17 embodiment, the needed force F for urging transducer 22 against the pinna P on each side of the head is provided by a single flexure 20. According to an embodiment of the present disclosure, frames 24 used in headband 30 are mirror images of each other, both attached to flexure 20, each frame 24 provided with its own circuit board 34. Power can be provided by a common external power source 48, with power supplied to a first circuit board, then routed along a cable to the second circuit board.

It can be appreciated that embodiments of the present disclosure described herein are suited to specific requirements for ultrasound signal generation, control, and placement for stimulation of the auricular vagus nerve and address the difficulty that is posed by the inability of the human user to detect or sense the presence of an ultrasound signal transmitted against the skin. Apparatus described herein can be utilized for transducer component positioning to deliver other types of stimulating signals to the pinna, such as electrical signals, heat, or acoustical vibration in the audible range, for example, in conjunction with the ultrasound stimulation or in place of ultrasound.

According to an alternate embodiment of the present disclosure, the design of headset apparatus 10 can also be adapted for use with electrical stimulation to pinna P and surrounding tissue. The component arrangement of FIG. 3, employing the constraint pattern of FIG. 2, can be used to urge one or more electrodes against the pinna P surface at contact surface C2, with suitable nesting force F from flexure 20, extended from contact surface C2 to contact surface C3. Alignment feature 28 of frame 24 can include an additional electrode that seats within ear canal C1. Electrical current can then be provided between electrodes for stimulation of the vagus nerve at the ear. A coupling fluid containing cannabinoids can be applied to both coupling pads in the dual transducer systems to improve ultrasonic coupling and chemical therapy.

A range of electrical signal levels and frequencies can be used to obtain therapeutic effects from electrical stimulation at pinna P. The stimulating signal can be DC, pulsed DC, or AC current, for example. Electrical stimulation can be combined with ultrasound stimulation, as described hereinabove, for increased therapeutic effect, as well as to allow multiple uses for the headset apparatus 10.

This disclosure has been provided in detail and may have been described with particular reference to a suitable or presently preferred embodiment, but it will be understood that variations and modifications can be affected within the spirit and scope of the invention. For example, headset apparatus 10 can be incorporated for operation within a closed loop system that includes sensors for detecting conditions or patterns in user physiology. The presently disclosed embodiments are therefore considered in all respects to be illustrative and not restrictive. The scope of the invention is indicated by the appended claims, and all changes that come within the meaning and range of equivalents thereof are intended to be embraced therein.

We claim:

1. A headset apparatus adjustable for one or more users to wear comprising:

(a) an ultrasound transducer mounted to said apparatus, wherein said ultrasound transducer is configured to press against an ear of said one or more users;

(b) a cannabinoid-containing coupling fluid on a surface of said ultrasound transducer, wherein said cannabinoid-containing coupling fluid comprises at least one cannabinoid selected from the group consisting of cannabidiol (CBD), tetrahydrocannabinol (THC), and cannabinol, and wherein said cannabinoid-containing coupling fluid that facilitates transmission of ultrasonic energy into human skin while delivering said at least one cannabinoid to tissue at or near an auricular vagus nerve; and (c) a securing member configured to position said ultrasound transducer against the ear of said one or more users.

2. The headset apparatus of claim 1, wherein said cannabinoid-containing coupling fluid is a solution that contains cannabidiol (CBD), tetrahydrocannabinol (THC), cannabinol, or combinations thereof.

3. The headset apparatus of claim 1, wherein said cannabinoid-containing coupling fluid further comprises a vitamin, amino acid, peptide, essential oil, herbal extract, anti-inflammatory agent, analgesic, or combinations thereof.

4. The headset apparatus of claim 1, wherein said cannabinoid-containing coupling fluid is a solution that contains tetrahydrocannabinol (THC) with at least one carrier wherein said carrier is water, glycerine, or a combination of water, glycerine and one or more emulsifiers.

5. The headset apparatus of claim 1, wherein said cannabinoid-containing coupling fluid is a solution that contains cannabinol as a terpene.

6. The headset apparatus of claim 1, wherein said at least one cannabinoid of said cannabinoid-containing coupling fluid is in solution with at least a second component.

7. The headset apparatus of claim 6, wherein said at least one cannabinoid is in solution with one or more vegetable fluids.

8. The headset apparatus of claim 1, wherein said at least one cannabinoid is incorporated into a conformal pad that is selectively removable from said headset apparatus.

9. The headset apparatus of claim 8, wherein a *cannabis* infused conformal pad is selectively removable from said headset apparatus.

10. A method for using an adjustable headset apparatus for one or more users to wear comprising:

(a) providing an ultrasound transducer mounted to said headset apparatus, wherein said ultrasound transducer is configured to press against an ear of said one or more users;

(b) applying a cannabinoid-containing coupling fluid to a surface of said ultrasound transducer, wherein said cannabinoid-containing coupling fluid comprises at least one cannabinoid selected from the group consisting of cannabidiol (CBD), tetrahydrocannabinol (THC), and cannabinol, to facilitate transmission of ultrasonic energy into human skin; and (c) delivering said at least one cannabinoid to tissue at or near an auricular vagus nerve during application of ultrasound energy.

11. The method of claim 10, wherein said cannabinoid-containing coupling fluid is a solution that contains cannabidiol (CBD), tetrahydrocannabinol (THC), cannabinol, or combinations thereof.

12. The method of claim 10, wherein said cannabinoid-containing coupling fluid further comprises a vitamin, amino acid, peptide, essential oil, herbal extract, anti-inflammatory agent, analgesic, or combinations thereof.

13. The method of claim 10, wherein said cannabinoid-containing coupling fluid is a solution that contains tetrahydrocannabinol (THC) with at least one carrier wherein said carrier is a gel, water, glycerine, or a combination of gel, water, glycerine and one or more emulsifiers.

14. The method of claim 10, wherein said cannabinoid-containing coupling fluid is a solution that contains cannabinol as a terpene.

15. The method of claim 10, wherein said at least one cannabinoid of said cannabinoid-containing coupling fluid is in solution with at least a second component.

16. The method of claim 15, wherein said at least one cannabinoid is in solution with one or more vegetable fluids.

17. The method of claim 16, wherein a *cannabis* containing fluid is incorporated or infused into a conformal pad.

18. The method of claim 17, wherein said user of said *cannabis* conformal pad can selectively remove said conformal pad from said apparatus.

* * * * *